United States Patent [19]

Sugiyama et al.

[11] Patent Number: 4,704,536
[45] Date of Patent: Nov. 3, 1987

[54] GAS SENSOR AND GAS DETECTING METHOD

[75] Inventors: Tadashi Sugiyama, Sagamihara; Yukio Yamauchi, Atsugi, both of Japan

[73] Assignee: Hochiki Corporation, Tokyo, Japan

[21] Appl. No.: 682,778

[22] Filed: Dec. 18, 1984

[30] Foreign Application Priority Data

Dec. 23, 1983 [JP] Japan .................................. 58-243192

[51] Int. Cl.$^4$ .............................................. G01N 23/00
[52] U.S. Cl. .................................... 250/381; 250/384; 324/469
[58] Field of Search ............... 250/381, 379, 384, 382, 250/385, 389, 375; 340/632; 324/469

[56] References Cited

U.S. PATENT DOCUMENTS

| | | | |
|---|---|---|---|
| 2,968,730 | 1/1961 | Morris et al. | 250/379 |
| 3,028,490 | 4/1962 | Guilleux | 250/381 |
| 3,361,908 | 1/1968 | Petitjean et al. | 250/252.1 |
| 3,665,441 | 5/1972 | Suchomel et al. | 250/385 |
| 3,735,138 | 5/1973 | Rork et al. | 250/375 |
| 4,280,052 | 7/1981 | Solomon | 250/381 |

Primary Examiner—Carolyn E. Fields
Attorney, Agent, or Firm—Lackenbach, Siegel, Marzullo & Aronson

[57] ABSTRACT

A gas sensor and a method for detecting a small amount of a gas such as CO contained in air entering a space between electrodes ionized by a radiation source. At least one radiation source is provided for ionizing at least a part of the space between the electrodes disposed so as to oppose each other and a radio d/x of a distance d cm between the electrodes to a field strength x V/cm of the ionized space is set to be 0.4 or more so as to obtain a change in the ionic current sufficient to realize gas sensing based on the formation of cluster ions within the ionized space.

7 Claims, 11 Drawing Figures

GAS SENSOR AND GAS DETECTING METHOD

BACKGROUND OF THE INVENTION

1. Field of the Invention

This invention relates to a gas sensor and a method for detecting a gas such as CO gas contained in a small amount in air flowing into a space between electrodes which is ionized by a radiation source.

2. Description of Prior Art

Heretofore, there has been known an inoization type smoke sensor which detects presence of aerosol (small particles suspended in air) entering a space between a pair of electrodes inonized by a radiation source. For example, U.S. Pat. No. 3,521,263 issued July 21, 1970 to Thomas Lampart and Andreas Scheidweiler proposes that a field strength of the ionized space be 5 V/cm or less to easily detect a combustion gas (aerosol) produced by a fire.

On the other hand, development of a gas sensor which is capable of detecting a deoxidizing gas such as CO, $H_2$, etc. arises recently, and there has been proposed a gas sensor which detects a gas such as CO contained in a small amount in air with a detecting mechanism similar to that of the conventional ionization type smoke sensor.

However, the mass of a gas molecule such as CO is as small as 1/10,000 of that of the aerosol (smoke particles), object of detection in the conventional smoke sensor. The detection of small gas molecule such as CO cannot be attained by mere selection of the field strength 5 V/cm as suggested in the U.S. Patent.

SUMMARY OF THE INVENTION

The present invention has been achieved based on the consideration of not only the field strength between the electrodes but the distance between the electrodes. More specifically, based on the inventors' confirmation that gas molecules gather together to form cluster ions when the gas molecules enter the electric field space ionized by a radiation source, the inventors have found out an appropriate relationship between the distance between the electrodes and the field strength which is suited for the produced cluster ions.

It is therefore an object of the present invention to provide a gas sensor and a gas detecting method which is capable of detecting a small amount of a gas such as CO contained in air based on a change in an ionic current caused by the gas molecules, with a detecting mechanism similar to that of the conventional smoke sensor, by selecting the ratio of the distance between the electrodes to the field strength of the space between electrodes.

According to the present invention, there is provided a gas sensor having two electrodes disposed oppositely each other and at least one radiation source for ionizing at least a part of a space between said electrodes for detecting a small amount of a gas such as CO gas contained in air entering the ionized space between the electrodes, which sensor is characterized in that the ratio d/x of a distance dcm between the electrodes to a field strength x V/cm of said ionized space is set to be 0.4 or more.

PREFERRED EMBODIMENTS OF THE INVENTION

Preferred embodiments and principle of the invention will now be described.

For easy understanding of the invention, a conventional ionization type smoke sensor will be first described.

Figure 10:
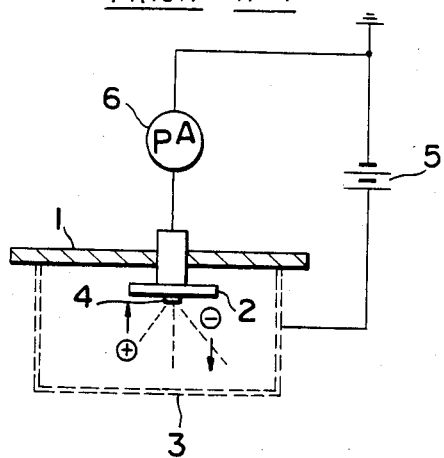
FIG. 10 is an explanatory view of a basic chamber structure of a conventional ionization type smoke sensor.

FIG. 10 illustrates a basic structure of a conventional ionization type smoke sensor. Oppositely charged electrodes 2 and 3 are mounted on an insulator 1 so as to oppose each other. A radiation source 4 comprising americium (Am 241) is provided on the inner electrode 2 so as to ionize the gas in a space between the electrodes. A d.c. voltage is applied between the electrodes 2 and 3 by a d.c. power source 5 to provide an electrical field in the space between the electrodes.

When aerosol produced, e.g. by combustion enters the d.c. electric field between the electrodes 2 and 3, molecular ions of air or electrons ionized by the radiation source 4 are adsorbed by the entering aerosol and reduction the ionic current between the electrodes 2 and 3 is measured by an ampere meter 6. The presence of aerosol can be detected by the reduction of the ionic current.

However, as the particles of a gas such as CO are extremely fine as described above, it is difficult to detect the presence of the gas.

In comparison with the conventional ionization type smoke sensor, a preferred embodiment of the present invention will now be described referring to FIG. 1.

Electrodes 10 and 11 are oppositely disposed and arranged in parallel with each other with a space d therebetween. The electrode 10 has a radiation source 12 such as americium on the face thereof which opposes to the electrode 11 so that gases in a space between the electrodes 10 and 11 are ionized by radiation of α-rays. A d.c. voltage is applied between the electrodes 10 and 11 by a d.c. power source 13 to form an electric field having a predetermined field strength. 14 is an ampere meter for detecting an ionic current flowing between the electrodes 10 and 11. The ampere meter 14 is a picoammeter which can detect a current on the order of picoampere.

Figure 1:
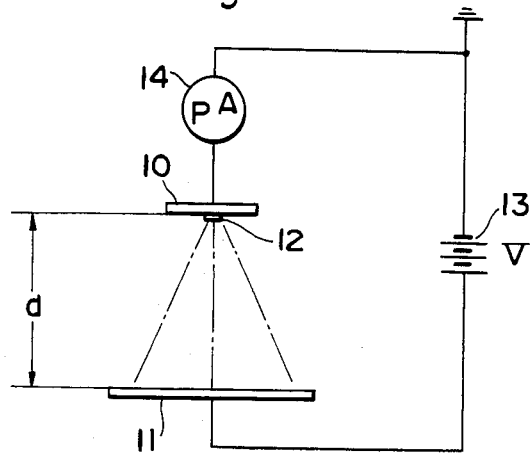
FIG. 1 is an explanatory view of a basic formation of one embodiment of the present invention.

In the gas detecting structure according to the present invention, as shown in FIG. 1, the ratio of the distance dcm between the electrodes 10 and 11 to the field strength x v/cm between the electrodes 10 and 11 is set as:

$d/x \geq 0.4$.

Figure 2:
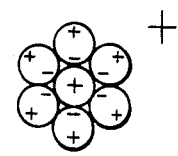
FIG. 2 is an explanatory view which schematically shows cluster ions formed in an ionized space.

Under these conditions, gases such as CO gas which enter the space between the electrodes 10 and 11 are ionized by the radiation source 12 and cluster ions schematically shown in FIG. 2 are formed. Each of the cluster ions is considered to be an aggregate of several or several tens of molecular ions, but it apparently behaves as a single ionized molecule.

The cluster ions thus formed when the gases such as CO gas etc. enters the space, have an effective ion radius larger than that of ordinary air components such as $N_2^+$ and $O_2^+$ ions. For this reason, the speed of migration of the cluster ions is low and the recombination probabilities are increased. In this connection, it is to be noted that the cluster ions are described in detail in "Ionized Gasses" by A. von Engel.

The presence of the cluster ions, which enables gas molecules to be detected by the gas sensor according to the present invention, is proved by the following experiment.

Figure 3:
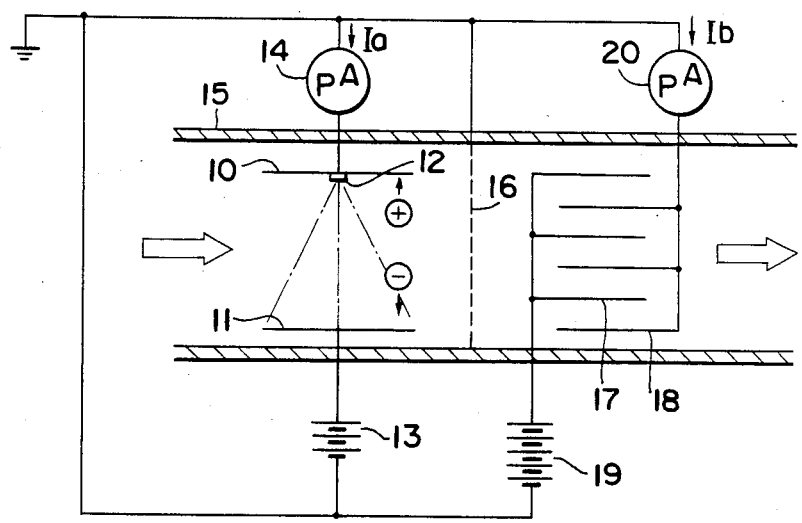
FIG. 3 is an explanatory view of one example of a device for conducting an experiment for proving the presence of the cluster ions.

FIG. 3 shows one example of a device for conducting the experiment to prove that cluster ions are formed in an electric field which is ionized by a radiation source. The chamber of a gas sensor according to the present invention, which comprises the electrodes 10 and 11 and the radiation source 12 as shown in FIG. 1, is provided on the entrance side of a wind tunnel 15 of an insulator. A d.c. voltage is applied between the electrodes 10 and 11 by the d.c. power source 13. The ampere meter 14 is provided to detect ionic current between the electrodes 10 and 11. A grounded wire mesh 16 is provided on the downstream side of the electrodes 10 and 11. Interdigital electrodes 17 and 18 are provided on the downstream side of the wire mesh 16. A d.c. voltage is applied between the electrodes 17 and 18 by a d.c. power source 19. A picoammeter 20 is provided to detect an ionic current flowing through the electrodes 17 and 18.

The experiment for proving the presence of the cluster ions using the device as shown in FIG. 3 is conducted as follows:

Voltages are applied by the d.c. power sources 13 and 19 between the electrodes 10 and 11 and between the electrodes 17 and 18, respectively. As a result, an ionic current Ia whose amount is determined by the ionization degree of the air molecules enters between the electrodes 10 and 11.

In this state, air is fed into the wind tunnel 15 in the direction of arrow. When the wind velocity exceeds a certain value, some of ions (the majority thereof are $N_2^+$ and $O_2^+$) of gas molecules produced between the electrodes 10 and 11 are blown away to between the electrodes 17 and 18 disposed on the downstream side. As a result, an ionic current Ib begins to flow between the electrodes 17 and 18 and the current is detected by the ampere meter 20.

Thus, the critical wind velocity V at which the ionic current between the electrodes 17 and 18 on the downstream side begins to flow is known. Subsequently, air containing CO gas is fed at a wind velocity lower than the critical wind velocity Va, and there is caused a change in the ionic currents as shown in FIG. 4(A).

More specifically, FIG. 4(A) shows the ionic currents after and before CO gas is supplied the wind velocity V=0.2 cm/sec. Before the CO gas is supplied, the ionic current Ia is constantly 55 picoameperes between the electrodes 10 and 11 and the ionic current Ib is substantially 0 picoampere between the electrodes 17 and 18. However, after CO gas is supplied, the ionic current Ia between the electrodes 10 and 11 is lowered to 30 picoamperes.

When the CO gas is supplied at a wind velocity e.g. Va=0.3 cm/sec which is higher than the critical wind velocity Va, there is caused a change in the ionic current as shown in FIG. (B). More specifically, when the CO gas is supplied at a wind velocity higher than the critical wind velocity Va, the ionic current between the electrodes 10 and 11 is lowered from 55 picoamperes to 30 picoamperes and the ionic current Ib between the electrodes 17 and 18 on the downstream side is increased from 0.30 picoampere to 0.35 picoampere.

Figure 4:
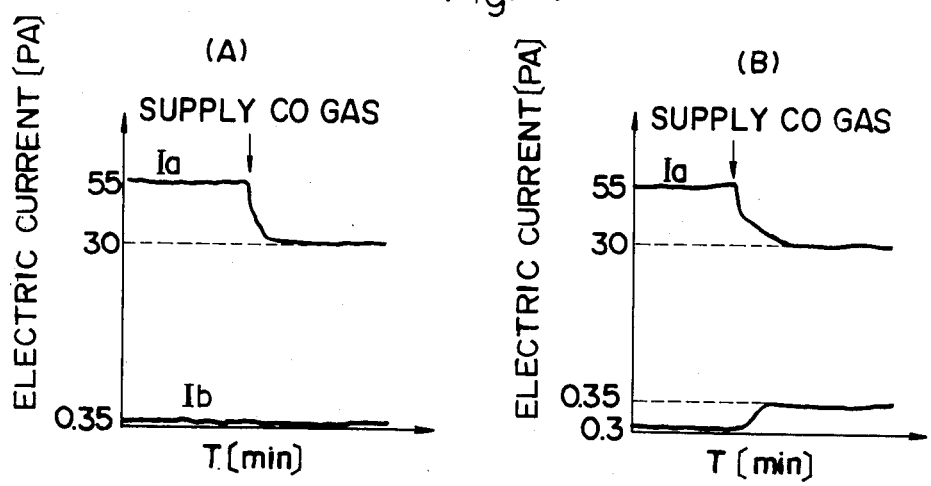
FIG. 4 is a graph showing a change in an ionic current due to the cluster ions.

From the experimental data as shown in FIG. 4, the presence of the cluster ions can be proved as follows:

If it is assumed that a certain ion which is affectable by the wind velocity more easily than the air molecular ion ($N_2^+$, $O_2^+$) is produced by supplying the CO gas, the reason why the newly produced ion is affected easily by the wind velocity is that the migration velocity k of the ion is small. The velocity k of the migration of the ion is substantially in inverse proportion to the effective radius of the ion. If the newly produced ions were all constituted of simple body molecular ions $CO-^+$ alone, they could not bring a change in the ionic current Ib between the electrodes 17 and 18 on the downstream side by the increase of the wind velocity, because they have an effective radius substantially the same as or even smaller than that of the air molecular ions $N_2^+$, $O_2^+$. However, as apparent from FIG. 4(B), the ionic current Ib between the electrodes on the downstream side is increased by the feeding of the CO gas and this shows that the cluster ions having an effective radius larger than the simple body molecular ions of the CO gas are produced and blown away into the downstream side.

The generation of the cluster ions can be seen not only with the CO gas but also with $H_2$ gas.

The mobility of an ion will now be described theoretically.

Between two sufficiently large, parallel electrodes, when gases between the electrodes are uniformly ionized by some appropriate radiation source, ion pairs of positive and negative ions produced between the electrodes migrate to the electrodes of opposite polarities, respectively. In the migration of the ion pairs, some of the ion pairs allow an ionic current to flow and others collide each other to be neutralized and recombined.

When the migration of the ions making the ionic current and the recombination come into an equilibrium state after a lapse of time, the number of ion pairs produced and the number of ion pairs disappeared are equal to each other in the equilibrium state and the numbers of the negative and positive ions of the pairs are equal. These relationships can be expressed as follows:

$$N^+ = N^- = N \tag{1}$$

wherein N is an ion density.

The rate of neutralization caused by the collision of the positive and negative ions is in proportion to $N^2$. If the number of the ion pairs produced every second per unit volume (cm$^3$) is assumed as $dN/dt$, the following equation can be obtained.

$$dN/dt = -\rho N^2 \tag{2}$$

wherein $\rho$ is a recombination coefficient

If the current flowing per unit area of a section of a space between the electrodes is expressed in the term of a current density j, the following equation can be obtained.

$$j = j^+ + j^- = e(N^+ v^+ + N^- v^-) = eN(v^+ + v^-) \quad (3)$$

wherein e is an electric charge and $v^+$ and $v^-$ are migration velocities of the positive and negative ions. respectively.

The migration velocity v of the ions as given by the formula (3) is in proportion to the field strength x.

$$v = kx \quad (4)$$

wherein k is mobility.

From the formulae (2),(3) and (4), the following formula can be obtained.

$$j = \{(k^+ + k^-) \, e[(dN/dt)\rho]^{\frac{1}{2}}\} x \quad (5)$$

In the formula (5), e, x, and dN/dt are constants which are not varied by the CO gas ions. The relationship between the recombination coefficient $\rho$ and the mobility k in a gas at an atmospheric pressure is given by the following formula:

$$\rho = 4\pi e(k^+ + k^-) \quad (6)$$

Thus, the item in the formula (5) which is varied by the presence of the CO ions is the mobility k. The mobility k is affected by the effective radius of the molecular ion and it decreases as the radius increases.

When a gas such as CO gas which is liable to form cluster ions is present even in a small amount, in the ionized gas between the electrodes, cluster ions are generated. As the effective radius of the generated cluster ions is large, the mobility k is lowered and ionic current j is also decreased due to the lowering of the mobility k.

The reason why the ratio cm d/x of the distance d between the electrodes and the field strength x v/cm is determined to be 0.4 or more when the cluster ions are produced as a result of the feeding of CO or $H_2$ gas which has been substantiated by the experiment conducted by using the device of FIG. 3 will be explained. The aerosol to be detected by the conventional ionization type smoke sensor has a mass as large as 10,000 times those of the air molecular ions. By this reason, the mobility of the aerosol by which the air molecules are adsorbed is so small that they can be regarded as standing as compared with the mobility of the air molecular ions. More specifically, in the ionization type smoke sensor, some of the air molecular ions generated are adsorbed by the aerosol and the resultant particles are substantially in the standing state, as the substantial number of the ion pairs is substantially decreased, and therefore the ionic current is decreased. Such decrease in the ionic current caused as mentioned above, is hardly influenced by the structure of the chamber or strength of the electric field and can be relatively easily detected.

In contrast, the cluster ions formed of the ionized CO gas has a mass several times or several tens of times that of the air molecular ion and the difference between the migration velocity of the cluster ions and the migration velocities of the air molecular ions such as $N_2^+$, $O_2^+$ is not so large as compared with the difference between the aerosol and the air molecular ions.

In other words, the cluster ions has a migration velocity which is not so high as that of the air molecular ions but which is a considerably high velocity in a general sense. By this reason, a gas such as CO etc. cannot be detected with a conventional chamber structure of the ionization smoke sensor. To detect the cluster ions, there is proposed a chamber structure which satisfies the following two requisites in combination:

(a) The field strength x in the space between the electrodes is made as small as possible to lower the velocity v of the migration of the ions. Refer to formula (4); and (b) The distance d between the electrodes is made as large as possible.

More particularly, it is effective for causing a large change in the ionic current to increase the time T during which the cluster ions stay in the space between the electrodes to increase the probabilities of recombination. The time T during which the cluster ions stay between the electrodes is expressed as follows:

$$T = d/v = d/kx \quad (7)$$

This equation can be converted into:

$$d/x = T \cdot K = R \quad (8)$$

If the ratio R of the distance d between the electrodes to the field strength x in the formula (8) is made as large as possible, the rate of change in the ionic current, i.e. the sensitivity with respect to the CO gas is increased.

Figure 5:
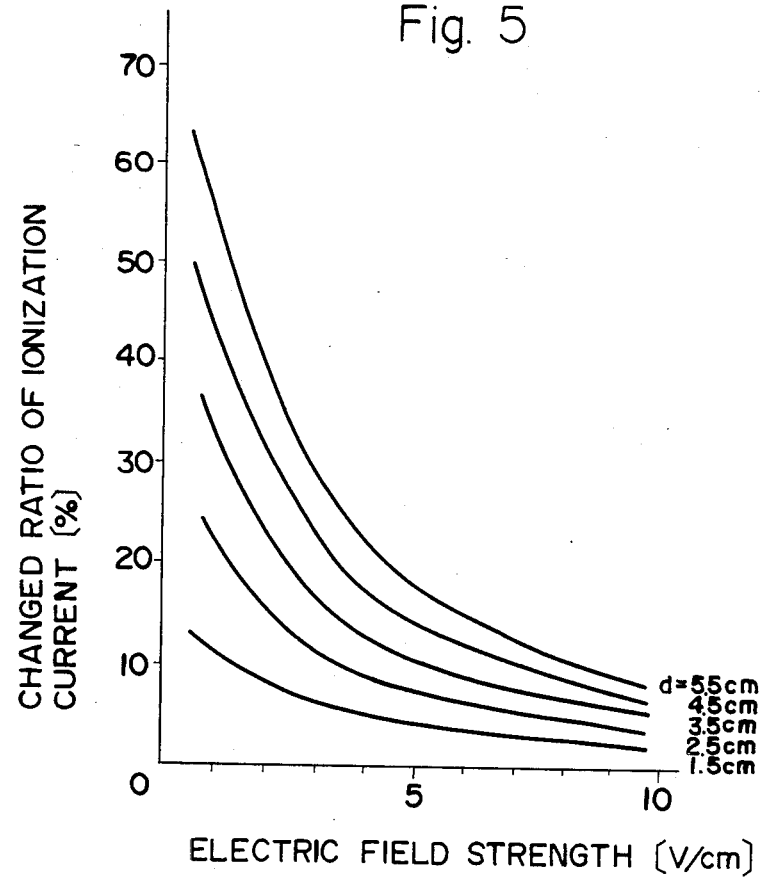
FIG. 5 is a graph showing a rate of change in the ionic current in relation with a field strength with a parameter of a distance between the electrodes.

FIG. 5 is a graph which shows the change rate of the ionic current in relation with the field strength with a parameter of the distance d between the electrodes when the sensor structure of FIG. 1 is used. CO gas of 100 ppm is injected.

Figure 6:
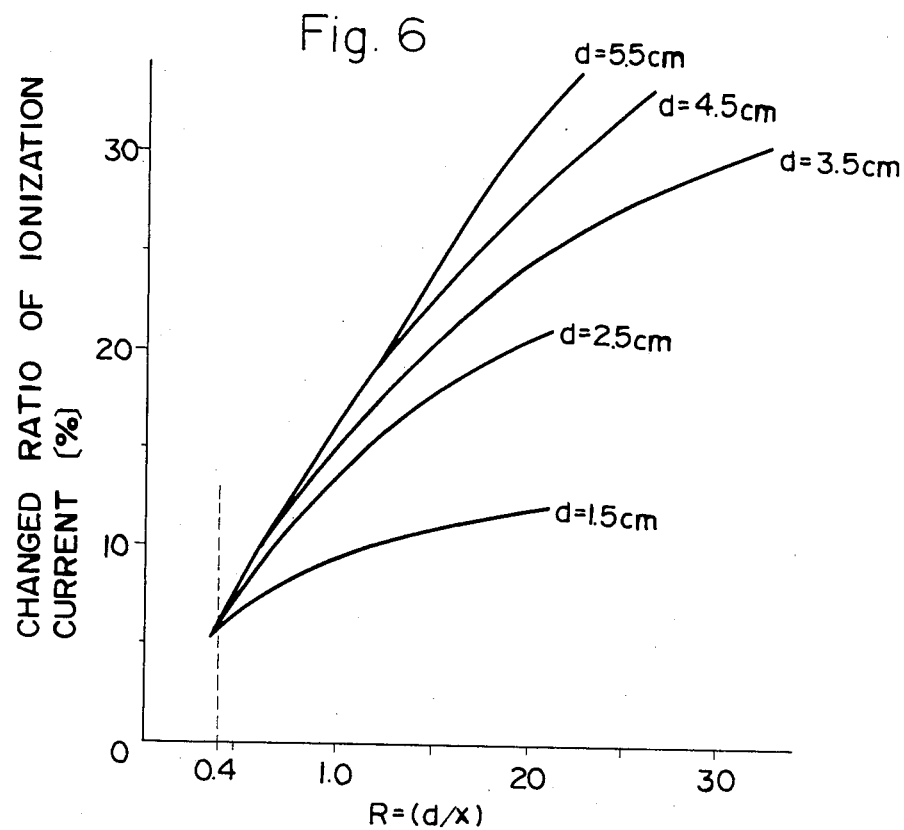
FIG. 6 is a graph showing the rate of change in the ionic current in relation with the ratio of the distance between the electrodes to the field strength with a parameter of the distance between the electrodes.

As apparent from the graph of FIG. 5, the change rate of the ionic current becomes larger as the distance d is increased and the change rate of the ionic current becomes larger as the field strength is lowered when the distance d between the electrodes is fixed. The change rate of the ionic current in relation with the ratio R of the distance d between the electrodes and the field strength x as given by formula (8) can be expressed as in FIG. 6 on the basis of the graph of FIG. 5. In FIG. 6, the distance d between the electrodes is also used as a parameter.

In this connection, it is to be noted that 10% or more of change rate in the ionic current is ideally desired and at least 5% of change rate in the ionic current is actually required to effectively detect 100 ppm of CO gas. Therefore, as apparent from the graph of FIG. 6, to realize a gas sensor for CO gas or $H_2$ gas, the ratio R of the distance dcm between the electrodes and the field strength xcm should be:

$$R = d/x \geq 0.4.$$

Figure 7:
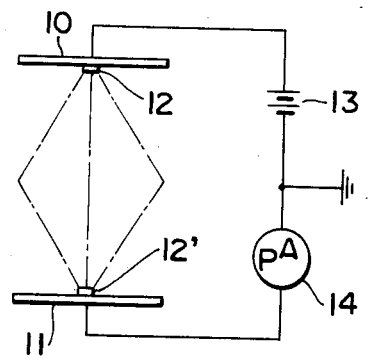
FIGS. 7, 8 and 9 are explanatory views of other embodiments of the present invention.

FIG. 7 illustrates another embodiment of the present invention. This embodiment is characterized in that the distance d between the electrodes is enlarged to enhance the detection sensitivity.

The distance d between the electrodes 10 and 11 is restricted by the effective reachable distance of the radiation by the radiation source 12 provided on the electrode 10. When americium (Am 241) is used as a radiation source 12, the effective reachable distance is about 4 cm. In this embodiment, therefore, another radiation source 12' is additionally provided on the opposite electrode 11 to double the effective reachable distance and to increase the distance d between the electrodes 10 and 11.

Figure 8:
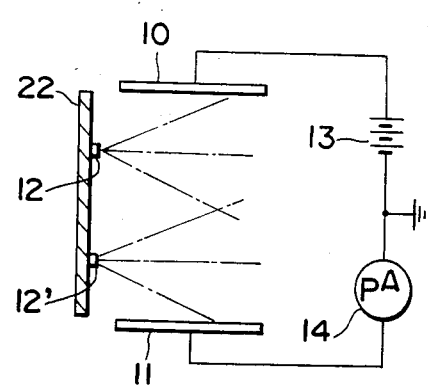

FIG. 8 shows a further embodiment of the present invention in which two radiation sources 12 and 12' are mounted on an insulator 22 disposed at a sideward position of the electrodes 10 and 11 which are arranged oppositely to each other, so as to uniformly ionize gases in the space between the electrodes 10 and 11 by the sideward radiation from the sources 12 and 12' and to enlarge the distance d between the electrodes 10 and 11.

Figure 9:
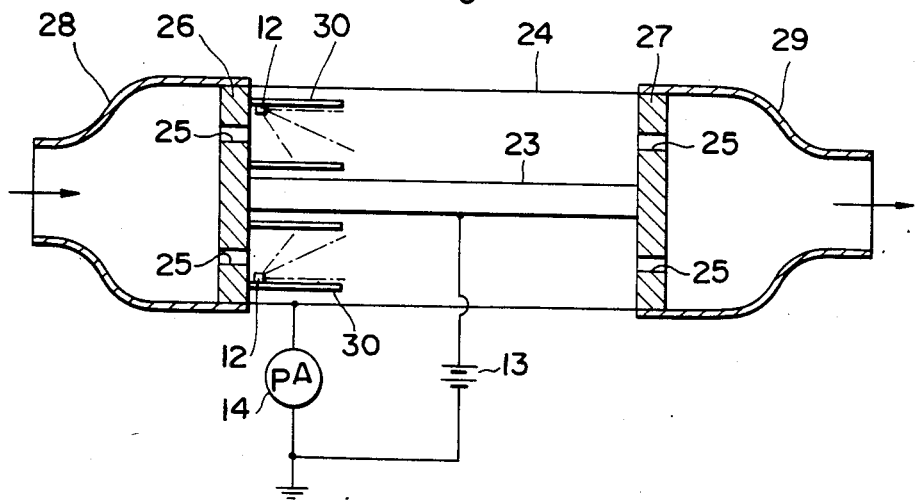

FIG. 9 illustrates a still further embodiment of the present invention. In this embodiment, a central electrode cylinder 23 and an outer electrode cylinder 24 are disposed coaxially. Insulators 26 and 27 each having through holes 25 are provided on the opposite ends of the central and outer electrodes 23 and 24. A suction cylinder 28 through which air to be monitored is let in is provided to the insulator 26 and a discharge cylinder 29 for discharging the air is provided to the insulator 28. A radiation shielding cylinder 30 is provided on the electrode side of the insulator 26 and a radiation source 12 is provided inside the radiation shielding cylinder 30. A d.c. power source 13 is provided to apply a d.c. voltage between the central and outer electrode cylinders 23 and 24. The resultant ionic current is detected by an ampere meter 14.

In the embodiment of FIG. 9, when CO and/or $H_2$ is contained in the air fed through the suction cylinder 28, ions produced in the space ionized by the radiation sources 12 are undergo formation of cluster ions and recombination of the ions during a course in which the ions pass through a space defined by the central and outer electrode cylinders 23 and 24. Thus a large change, namely remarkable decrease in the ionic current can be obtained. In this case, the substantial distance d is a vectorial sum of a migration distance of the ions in the direction of the electric field and the travel distance of the ions in the axial direction by the flow of the air.

The present invention can be realized in various further modes without departing the essential characteristic features of the present invention and it should not be limited to the embodiments as illustrated.

What is claimed is:

1. A gas sensor having two electrodes disposed oppositely each other and at least one radiation source for ionizing at least a part of a space between said electrodes, which sensor is characterized in that the ratio d/x of distance d cm between the electrodes to a field strength x V/cm of said ionized space is set to be 0.4 or more, the ratio being such that the sensor detects concentration as low as 100 p.p.m. of a gas of low density relative to air and which is contained in air entering the ionized space between the electrodes.

2. A gas sensor as claimed in claim 1 wherein said at least one radiation source is mounted on one of the electrodes.

3. A gas sensor as claimed in claim 1, wherein at least two radiation sources are provided and each is mounted on the respective electrodes, so as to permit the distance between the electrodes to be increased while maintaining the field strength of said ionized space at 0.4 v/cm or more.

4. A gas sensor as claimed in claim 1 wherein said at least one radiation source is disposed intermediate between the electrodes so as to radiate sidewardly into the space between the electrodes.

5. A gas sensor as claimed in claim 1 wherein said electrodes are a central electrode cylinder and an outer electrode cylinder, respectively, said central electrode cylinder and said outer electrode cylinder being disposed coaxially with each other, said gas sensor further comprising insulators with through openings mounted on the opposite ends of the electrode cylinders, a suction cylinder and a discharge cylinder which are fitted to said insulators, respectively, and a radiation shielding cylinder provided on one of said insulators to which said suction cylinder is fitted on the electrode side thereof and containing said at least one radiation source therein.

6. A gas detecting method comprising ionizing at least a part of a space between two electrodes disposed so as to oppose each other and detecting concentrations as low as 100 p.p.m. of a gas of low density relative to air and which is contained in air entering the ionized space, which method is characterized in that the ratio d/x of the distance dcm between the electrodes to the field strength x V/cm of said ionized space is set at 0.4 or more.

7. A gas detecting method in accordance with claim 6, wherein said gas is from the class consisting of hydrogen and carbon monoxide.

* * * * *